United States Patent
Mizushima

(10) Patent No.: US 7,709,430 B2
(45) Date of Patent: May 4, 2010

(54) CLEANSING COMPOSITION

(75) Inventor: Hiroki Mizushima, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/917,413

(22) Filed: Aug. 13, 2004

(65) Prior Publication Data

US 2005/0049169 A1  Mar. 3, 2005

(30) Foreign Application Priority Data

Aug. 22, 2003  (JP) ............................. 2003-298058

(51) Int. Cl.
*A61K 7/00* (2006.01)
(52) U.S. Cl. ................. 510/123; 510/124; 510/125; 510/127; 510/128
(58) Field of Classification Search ............... 510/119, 510/122, 123, 125, 127; 424/70.1
See application file for complete search history.

(56) References Cited

U.S. PATENT DOCUMENTS

| | | | | |
|---|---|---|---|---|
| 5,955,066 | A * | 9/1999 | Sako et al. | 424/70.12 |
| 6,133,212 | A * | 10/2000 | Elliott et al. | 510/159 |
| 6,191,083 | B1 * | 2/2001 | Brooks et al. | 510/124 |
| 6,444,629 | B1 * | 9/2002 | Elliott et al. | 510/131 |
| 6,696,052 | B2 * | 2/2004 | Aeby et al. | 424/70.122 |
| 6,737,050 | B2 * | 5/2004 | Doi et al. | 424/70.27 |
| 2002/0031532 | A1 * | 3/2002 | Uchiyama | 424/401 |
| 2006/0166845 | A1 * | 7/2006 | Terada | 510/127 |

FOREIGN PATENT DOCUMENTS

| | | | |
|---|---|---|---|
| EP | 0 855 178 A2 | | 7/1998 |
| EP | 1329214 | * | 7/2003 |
| JP | A-S56-072095 | | 6/1981 |
| JP | A-H01-128914 | | 5/1989 |
| JP | A-10-203932 | | 4/1998 |
| JP | A-H10-182368 | | 7/1998 |
| JP | A-2000-038326 | | 8/2000 |

* cited by examiner

*Primary Examiner*—Necholus Ogden, Jr.
(74) *Attorney, Agent, or Firm*—Oblon, Spivak, McClelland, Maier & Neustadt, L.L.P.

(57) ABSTRACT

A cleansing composition containing the following components (A) to (C):
(A) an anionic surfactant
(B) a copolymer of a dialkyl diallyl ammonium salt/acrylamide
(C) fatty acid alkanolamide and/or polyoxyethylene alkyl ether,
wherein pH at 25° C., in 20 weight times water dilution, is 2 to 4.5.

The present cleansing composition has a good foamability in hair washing, a fine-textured and soft foam quality, and in particular, a good smoothness in rinsing and lasting the smoothness longer in rinsing.

21 Claims, No Drawings

CLEANSING COMPOSITION

FIELD OF THE INVENTION

The present invention relates to a cleansing composition with low pH, containing a cationic polymer.

BACKGROUND OF THE INVENTION

Hair is liable to become dry and coarse by environmental factors such as daily exposure to UV ray or heat from the sunlight, along with physical factors such as hair washing, brushing and heating with a dryer. Furthermore, recently hair dying or hair styling has become a trend for personal pleasure and thus, with increasing frequency of coloring and permanent treatment, hair tends to be damaged, lose gloss as well as elasticity and smoothness, and consequently becomes dry and less manageable in styling. In particular, the smoothness of hair in washing is significantly reduced, resulting in further poorer texture feeling during rinsing after lathering such as being crunchy, tangling etc.

To attain smoother feeling of hair in washing, various cationic polymers have generally been added into haircleansing compositions. Examples include; a shampoo composition superior in conditioning effect by a combined use of a cationic polymer and silicone derivatives (JP-A-56-72095), a shampoo composition providing smooth feeling, having a certain pH range and containing a specific anionic surfactant, an amphoteric surfactant and a cationic polymer (JP-A-10-182368) and a shampoo composition superior in texture feeling and conditioning effect by a combined use of a copolymer of a dialkyl diallyl ammonium salt and cationic cellulose (JP-A-1-128914).

However, conventional technologies have not been sufficient for an excessively damaged hair, which is often seen recently, to attain smoothness of hair during lathering and rinsing.

SUMMARY OF THE INVENTION

The present invention provides a cleansing composition containing the following components (A) to (C):
(A) an anionic surfactant
(B) a copolymer of a dialkyl diallyl ammonium salt/acrylamide
(C) fatty acid alkanolamide and/or polyoxyethylene alkyl ether, wherein the composition has a pH of 2 to 4.5 at 25° C, in 20 weight times water dilution.

DETAILED DESCRIPTION OF THE INVENTION

The present invention relates to a cleansing composition providing a fine-textured and soft foam quality, lathering quickly and abundantly, a good smoothness of hair during rinsing and lasting the good smoothness of hair to the end of rinsing even in a excessively damaged hair.

The present inventors have found that the above-described requirements can be satisfied by a cleansing composition having low pH and containing an anionic surfactant, a specific cationic polymer and a specific nonionic surfactant.

The anionic surfactant (A), includes compounds having sulfuric acid residues, sulfonic acid residues and carboxylic acid residues. Examples of the anionic surfactant include polyoxyethylene alkylether sulfate salt, polyoxyethylene alkenylether sulfate salt, alkyl sulfate salt, polyoxyalkylene alkylphenyl ether sulfate salt, alkyl sulfosuccinate salt, polyoxyalkylene alkyl sulfosuccinate salt, higher fatty acid salt and alkane sulfonic acid salt and the like. Among them, those represented by the following general formula (1) and (2) are preferable.

$$R^1O(CH_2CH_2O)_mSO_3M \quad (1)$$

$$R^2OSO_3M \quad (2)$$

(wherein $R^1$ represents an alkyl group or an alkenyl group having 10 to 18 carbon atoms; $R^2$ represents an alkyl group having 10 to 18 carbon atoms; M represents an alkali metal, an alkaline earth metal, ammonium, alkanol amine or basic amino acid; and m represents a number of 1 to 5 in weight average.)

The component (A) in the present invention may be used in combination of two or more types and the content thereof is preferably from 1 to 50% by weight, more preferably from 5 to 30% by weight, even more preferably from 8 to 25% by weight of the cleansing composition, from the viewpoint of foamability, easiness of handling in use and cleansing ability.

A copolymer of a dialkyl diallyl ammonium salt/acrylamide(B), is preferably a copolymer of a dimethyl diallyl ammonium halide/acrylamide. Weight ratio of a dialkyl diallyl ammonium salt to acrylamide is preferably 10:90 to 90:10 and more preferably 40:60 to 60:40. Weight average molecular weight thereof is preferably $0.5 \times 10^6$ to $3 \times 10^6$ and more preferably $1 \times 10^6$ to $2 \times 10^6$. Typically, Such copolymers include "Merquat 550", "Merquat S" and "Merquat2200" (all from ONDEO NALCO Ltd.).

The component (B) of the present invention may be used in combination of two or more types, and the content thereof is preferably from 0.01 to 1.0% by weight, more preferably from 0.03 to 0.5% by weight, even more preferably from 0.05 to 0.3% by weight of the cleansing composition, from the viewpoint of foamability, fine-textured and soft foam quality, a good smoothness of hair during rinsing and lasting the smoothness of hair to the end of rinsing.

A fatty acid alkanolamide (C), has preferably an acyl group having carbon atoms of 8 to 22, more preferably carbon atoms of 10 to 16. The fatty acid alkanolamide may be either one of monoalkanolamide ordialkanolamide, and preferably has a hydroxyalkyl group having carbon atoms of 2 to 3, and includes, for example, oleicdiethanolamide, palm kernel oil fatty acid diethanolamide, coconut fatty acid diethanolamide, lauric acid diethanolamide, polyoxyethylene coconut fatty acid monoethanolamide, coconut fatty acid monoethanolamide, lauric acid isopropanolamide and lauric acid monoethanolamide. Among these, the fatty acid monoalkanolamide is preferable and the coconut fatty acid monoalkanolamide is more preferred.

Polyoxyalkylene alkyl ethers (C), preferably have a linear or branched alkyl group having carbon atoms of 8 to 22, more preferably carbon atoms of 10 to 18. The number of moles of alkyleneoxide to be added is preferably 1 to 30 in weight average. Preferably, the polyoxyalkylene alkyl ether has HLB (a Griffin method) of from 7 to 18, more preferably 9 to 15.

The component (C) may be used in combination of two or more types. It is even more preferable to use both fatty acid alkanolamide and polyoxyethylene alkyl ether is preferred. The content of component (C) of the present invention is preferably from 0.1 to 10% by weight, more preferably from 0.3 to 5% by weight, and even more preferably from 0.5 to 4% by weight of a cleansing composition from the viewpoint of foamability, fine-textured and soft foam quality, a good smoothness of hair during rinsing and lasting smoothness of hair to the end of rinsing. In relation to content of component (B), weight ratio of component (B) to component (C) is preferably 1:50 to 1:5 and more preferably 1:40 to 1:6, from the viewpoint of hair in rinsing.

A cleansing composition of the present invention preferably further contains a cationic polymer (D) other than component (B). Component (D) includes, typically such as cationic cellulose derivatives, cationic starch, cationic guar gum derivatives, homopolymers of diallyl quaternary ammonium salt, quaternized polyvinylpyrrolidone derivatives, polyglycol polyamine condensates, copolymers of vinylimidazolium trichlorides/vinylpyrrolidone, copolymers of hydroxyethyl cellulose/dimethyldiallylammonium chloride, copolymers of vinylpyrrolidone/quaternized dimethylaminoethyl methacrylate, copolymers of polyvinylpyrrolidone/alkylamino acrylate, copolymers of polyvinylpyrrolidone/alkylamino acrylate/vinylcaprolactam, copolymers of vinylpyrrolidone/methacrylamidopropyl trimethylammonium chloride, copolymers of alkylacrylamide/acrylate/alkylaminoalkyl acrylamide/polyethylene glycol methacrylate, copolymers of adipic acid/dimethylaminohydroxypropyl ethylenetriamine ("Cartaretin" from Sandos Co., Ltd., USA), and cationic polymers disclosed in JP-A-53-139734 and JP-A-60-36407. Among them, cationic cellulose derivatives and cationic guar gum derivatives are preferred.

The content of component (D) of the present invention is preferably from 0.1 to 2% by weight, more preferably from 0.2 to 1.5% by weight, and even more preferably from 0.3 to 1% by weight of a cleansing composition, from the viewpoint of furnishing qualities such as smoothness of hair from lathering to rinsing of a cleansing composition, manageability after drying, a long-lasting fine-textured and soft foam quality and improved adsorption of effective ingredients onto hair. In relation to content of component (B), weight ratio of component (B) to component (D) is preferably 1:1 to 1:10 and more preferably 1:4 to 1:6.

In the cleansing composition of the present invention, one or more types of conditioning component (E) selected from a cationic surfactant, silicones and oils may be used to improve finishing performances after drying.

The cationic surfactant includes, for example, lauryl trimethyl ammonium chloride, cetyl trimethyl ammonium chloride, cetyl trimethyl ammonium bromide, stearyl trimethyl ammonium chloride, stearyl trimethyl ammonium bromide, lauryl trimethyl ammonium bromide, dialkyl dimethyl ammonium chloride, dicetyl dimethyl ammonium chloride, distearyl dimethyl ammonium chloride, dicocoyl dimethyl ammonium chloride, myristyl dimethyl benzyl ammonium chloride, stearyl dimethyl benzyl ammonium chloride, lanolin fatty acid aminopropyl ethyl dimethyl ammonium ethyl sulfate, lanolin fatty acid aminoethyl triethyl ammonium ethyl sulfate, lanolin fatty acid aminoethyl diethyl methyl ammonium ethyl sulfate, lanolin fatty acid aminoethyl trimethyl ammonium ethyl sulfate, lanolin fatty acid aminopropyl triethyl ammonium ethyl sulfate, lanolin fatty acid aminoethyl trimethyl ammonium methyl sulfate, lanolin fatty acid aminopropyl ethyl dimethyl ammonium methyl sulfate, isoalkanoic acid($C_{14}$-$C_{20}$) aminopropyl ethyl dimethyl ammonium ethyl sulfate, isoalkanoic acid($C_{18}$-$C_{22}$) aminopropyl ethyl dimethyl ammonium ethyl sulfate, isostearic acid aminopropyl ethyl dimethyl ammonium ethyl sulfate, isononanoic acid aminopropyl ethyl dimethyl ammonium ethyl sulfate and alkyl trimethyl ammonium saccharin. These cationic surfactants may be used in combination of two or more types and content thereof is preferably from 0.01 to 5% by weight, more preferably from 0.05 to 3% by weight, and even more preferably from 0.1 to 1% by weight of a cleansing composition from the viewpoint of smoothness of hair from lathering to rinsing, easiness to finger through and manageability after drying.

Silicones include the followings;

(Silicones-1) dimethylpolysiloxane, such as represented by the following general formula:

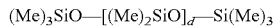

(wherein Me represents a methyl group and d represents a number of 3 to 20000.)

(Silicones-2) amino modified silicones

Various types of amino modified silicones may be used and among them, one described as "Amodimethicone" in the CTFA dictionary (Cosmetic Ingredient Dictionary, USA), the third edition, which has the average molecular weight of about 3000 to 100000, is preferable. This amino modified silicone is preferably used as aqueous emulsion and a commercially available product thereof includes "SM 8704C" (from Toray Dow Corning Silicone Co., Ltd.) and "DC 929" (from Dow Corning Co., Ltd.).

(Silicones-3) other silicones

Silicones other than the above-described types include polyether modified silicones, methyl phenyl polysiloxane, fatty acid modified silicones, alcohol modified silicones, alkoxy modified silicones, epoxy modified silicones, fluoride modified silicones, cyclic silicones and alkyl modified silicones. These silicones may be used in combination of two or more types and content thereof is preferably 0.1 to 7% by weight, more preferably 0.2 to 6% by weight and further preferably 0.3 to 5% by weight of a cleansing composition of the present invention from the view point of smoothness of hair from lathering to rinsing, easiness to finger through and manageability after drying.

Oils and fat include hydrocarbons such as squalene, squalane, liquid paraffines, liquid isoparaffines and cycloparaffines; glycerides such as castor oil, cacao oil, mink oil, avocado oil and olive oil; waxes such as bee wax, whale wax, lanolin and carnauba wax; alcohols such as myristyl alcohol, cetyl alcohol, oleyl alcohol, stearyl alcohol, isostearyl alcohol, 2-octyldodecanol and glycerine; esters such as isopropyl palmitate, isopropyl myristate, octyldodecyl myristate, hexyl laurate, cetyl lactate, propylene glycol monostearate, oleyl oleate, hexadecyl 2-ethylhexanoate, isononyl isononanoate and tridecyl isononanoate; higher fatty acids such as capric acid, lauric acid, myristic acid, palmitic acid, stearic acid, behenic acid, oleic acid, palm oil fatty acid, isostearic acid and isopalmitic acid; and others such as isostearyl glyceryl ether and polyoxypropylene butyl ether. Among these, esters are preferable and further, hexadecyl 2-ethylhexanoate, isononyl isononanoate and isopropyl palmitate are preferable. These oils and fat may be used in combination of two or more types and the content thereof is preferably from 0.1 to 7% by weight, more preferably from 0.2 to 6% by weight, and even more preferably from 0.5 to 5% by weight of a cleansing composition of the present invention, from the view point of smoothness of hair from lathering to rinsing, easiness to finger through and manageability after drying.

In the cleansing composition of the present invention, a nonionic surfactant (F) other than component (C) may be contained, to improve storage stability of a cleansing composition. Such nonionic surfactant includes, for example, polyoxyalkylene sorbitan fatty acid esters, polyoxyalkylene sorbit fatty acid esters, polyoxyalkylene glycerine fatty acid esters, polyoxyalkylene fatty acid esters, polyoxyalkylene alkyl phenyl ethers, polyoxyalkylene (hydrogenated) castor oil, sucrose fatty acid esters, polyglycerine alkyl ethers, polyglycerine fatty acid esters and alkyl glycosides. Among them, alkyl glycosides, polyoxyalkylene ($C_8$ to $C_{20}$) fatty acid esters, polyoxyethylene sorbitan fatty acid esters and polyoxyalkylene hydrogenated castor oil are preferred.

These nonionic surfactants may be used in combination of two or more types and the content thereof is preferably from 0.1 to 30% by weight, more preferably from 0.5 to 20% by weight and even more preferably from 1.0 to 10% by weight in a cleansing composition of the present invention, from the view point of storage stability of a cleansing composition, easiness of handling in use, lathering quickly and abundantly, easiness of hair wash and fine-textured and soft foam quality.

The cleansing composition of the present invention may further contain an amphoteric surfactant (G), to improve storage stability of the cleansing composition. The amphoteric surfactant includes betaine-type surfactant, in which alkyl a dimethylaminoacetic acid betaine and a fatty acid amidopropyl betainesare preferable, and the latter is more preferred. Fatty acid amidopropyl betaines preferably have an acyl group having carbon atoms of 8 to 18, more preferably carbon atoms of 10 to 16, and typical examples includelaurylamidopropyl betaine, palm kernelamidopropyl betaine and cocamidopropyl betaine.

The content of an amphoteric surfactant of the present invention is preferably from 0.1 to 10% by weight, more preferably from 0.2 to 8% by weight, and even more preferably from 2 to 6% by weight of the cleansing composition from the viewpoint of obtaining an good foam boosting effect.

The cleansing composition of the present invention, a solvent enhancing penetration into hair (H) may contain, to improve hair luster and manageability. The solvent enhancing penetration into hair includes aromatic alcohols, N-alkyl pyrrolidones, alkylene carbonates, polypropylene glycols, lactones and cyclic ketones. The aromatic alcohol includes benzyl alcohol, cinnamyl alcohol, phenetyl alcohol, p-anisyl alcohol, p-methylbenzyl alcohol, phenoxy ethanol and 2-benzyloxyethanol. The N-alkylpyrrolidone includes N-methyl pyrrolidone, N-octyl pyrrolidone and N-lauryl pyrrolidone. The alkylene carbonate includes a ethylene carbonate and a propylene carbonate. The polypropylene glycol preferably has a molecular weight of from 300 to 600 and a degree of polymerization of 2 to 5. Lactones preferably has a linear or branched alkyl group having carbon atoms of 1 to 6, such as a methyl group, an ethyl group, a propyl group, an isopropyl group and a butyl group, in which the alkyl group substitutes at γ-position in the case of γ-lactones, or at δ-position in the case of δ-lactones; that is, at methylene adjacent to a hetero oxygen atom. To increase water solubility of lactones, such lactones having acid residues such as sulfonic acid, phosphoric acid and carboxylic acid or an alkyl group substituted by these acid residues are preferred. The lactones include γ-butyrolactone, γ-caprolactone, γ-valerolactone, δ-valerolactone, δ-caprolactone and δ-heptanolactone. Among these, γ-lactones. In particular, δ-butyrolactone and δ-caprolactone are preferable in the view of stability of lactones. Cyclic ketones include cyclopentanone, cyclohexanone, cycloheptanone and 4-methylcycloheptanone.

The component (H) of the present invention may be used in combination of two or more types and the content thereof is preferably from 0.1 to 20% by weight, more preferably from 0.2 to 10% by weight, and even more preferably from 0.7 to 7% by weight of a cleansing composition, from the viewpoint of smoothness of hair from lathering to rinsing.

The cleansing composition of the present invention has pH of 2 to 4.5 at 25° C., in 20 times weight water dilution, preferably 2.5 to 4, and even more preferably 3 to 3.9 from the viewpoint of smoothness during rinsing, easiness to finger through and good texture feeling upon finishing. It is preferable to use organic acids having carbon atoms of not more than 8 for pH adjustment.

Organic acids having carbon atoms of not more than 8 are preferably dicarboxylic acids, tricarboxylic acids and hydroxycarboxylic acids. Typically, dicarboxylic acids include malonic acid, succinic acid, glutaric acid, adipic acid, maleic acid, fumaric acid, phthalic acid, oxalic acid, malic acid and tartaric acid, while tricarboxylic acids include citric acid, and hydroxy carboxylic acids include glycolic acid, lactic acid, malic acid, tartaric acid and citric acid. Among them, glycolic acid, lactic acid, malonic acid, maleic acid and malic acid are preferred. Salts thereof include ones with alkali metals, alkaline earth metals, ammonia and organic amine compounds.

These organic acids may be used in combination of two or more types and the content thereof is preferably from 0.1 to 5.0% by weight, more preferably 0.2 to 3.0% by weight, and even more preferably from 0.5 to 2.0% by weight so long as the pH lies within the above-described ranges from the viewpoint of improvement in finishing performances in terms of hair luster and manageability.

The cleansing composition of the present invention may further contain components those used in a general hair-wash other than the above-described ones may be added as appropriate, depending on the objectives. Such components include, for example, anti-dandruff agents; vitamins; disinfectants; anti-inflammatory agents; antiseptics; chelate agents; moisturizing agents such as solbitol and pantenol; coloring agents such as dye and pigments; viscosity adjusters such as hydroxyethyl cellulose, methyl cellulose, polyethylene glycol and clay mineral; pH adjusters such as potassium hydroxide; plant extracts; pearly-appearance agents; perfumes; colorants; UV absorbents; antioxidants; and other components listed in "ENCYCLOPEDIA OF SHAMPOO INGREDIENTS (MICELLE PRESS)".

A cleansing composition of the present invention is useful, in particular, as a hair-washing composition and preferably used in a bath room as a shampoo composition, a 2-in-1 shampoo and conditioner or the like, among which a shampoo composition is preferable.

EXAMPLES

The following examples further describe and demonstrate embodiments of the present invention; however, the scope of the present invention should not be limited thereto.

In the following Examples and Comparative Examples, pH is measured at 25° C., in 20 weight times water dilution.

Examples 1 to 3 and Comparative Examples 1 to 3

Shampoo compositions shown in Table 1 were prepared to be subjected to sensory evaluation.

(Evaluation Method)

Ten panelists applied each sample to a bundle of female hair of 20 g and about 30 cm long, which has been treated with hair bleaching once, followed by lathering and sufficient rinsing (for 15 seconds). Samples were ranked according to the average of evaluation points based on the following standards. Luster was evaluated after drying the hair bundle by comparison with a non-treated hair bundle (control hair).

(Evaluation Standard)

Foamability

4: excellent foamability
3: good foamability
2: relatively good foamability
1: relatively poor foamability
0: poor foamability Fineness of foam texture 4: excellent fineness
3: good fineness
2: relatively good fineness
1: relatively poor fineness
0: no fineness Softness of foam 4: excellent softness
3: good softness
2: relatively good softness
1: relatively poor softness
0: no softness Smoothness in the start of rinsing 4: excellent smoothness
3: good smoothness
2: relatively good smoothness
1: relatively poor smoothness
0: no smoothness Smoothness in the end of rinsing 4: excellent smoothness
3: good smoothness
2: relatively good smoothness
1: relatively poor smoothness
0: no smoothness Luster 4: better gloss in treated hair
3: relatively better gloss in treated hair
2: equivalent level of gloss between treated hair and control hair
1: relatively better gloss in control hair
0: better gloss in control hair (Ranking)

A: averaged evaluation point of 3.1 to 4.0
B: averaged evaluation point of 2.1 to 3.0
C: averaged evaluation point of 1.1 to 2.0
D: averaged evaluation point of 0 to 1.0

TABLE 1

| Component (% by weight) | Comparative Example | | | | | | Example | | |
| --- | --- | --- | --- | --- | --- | --- | --- | --- | --- |
| | 1 | 2 | 3 | 4 | 5 | 6 | 1 | 2 | 3 |
| (A): Sodium polyoxyethylene(2)lauryl ether sulfate | 10.0 | 10.0 | 10.0 | 10.0 | 10.0 | 10.0 | 10.0 | 10.0 | 10.0 |
| (A): Sodium lauryl sulfate | 5.0 | 5.0 | 5.0 | 5.0 | 5.0 | 5.0 | 5.0 | 5.0 | 5.0 |
| (B): Dimethyldiallyl ammonium chloride/ acrylamide copolymer liquid* | — | 1.5 | 1.5 | 1.5 | 1.5 | — | 1.5 | 1.5 | 1.5 |
| (C): Cocamide MEA | 0.8 | — | — | 0.8 | 0.8 | 0.8 | 0.8 | 0.8 | 0.8 |
| (C): Polyoxyethylene(16) lauryl ether | 2.0 | — | — | 2.0 | 2.0 | 2.0 | 2.0 | 2.0 | 2.0 |
| Lauramidopropyl betaine | 3.0 | 3.0 | 3.0 | 3.0 | 3.0 | 3.0 | 3.0 | 3.0 | 3.0 |
| Polypropyleneglycol (Mw = 400) | 1.0 | 1.0 | 1.0 | 1.0 | 1.0 | 1.0 | 1.0 | 1.0 | 1.0 |
| Polyquaternium-10 | — | — | — | — | 0.5 | — | — | 0.5 | 0.5 |
| Silicone emulsion with high molecular weight dimethylpolysiloxane | — | — | 2.0 | — | — | — | — | — | 2.0 |
| 48% by weight of a solution of sodium hydroxide | q.s.** | q.s.** | q.s.** | q.s.** | q.s.** | q.s.** | q.s.** | q.s.** | q.s.** |
| Malic acid | q.s.** | q.s.** | q.s.** | q.s.** | q.s.** | q.s.** | q.s.** | q.s.** | q.s.** |
| Purified water | Balance | Balance | Balance | Balance | Balance | Balance | Balance | Balance | Balance |
| pH (in diluted state by 20 times by weight with water, 25° C.) | 6.5 | 6.5 | 4.0 | 6.5 | 6.5 | 4.0 | 4.0 | 4.0 | 4.0 |
| Evaluation Foamability | B | B | C | B | B | B | B | A | A |
| | 2.8 | 2.6 | 1.7 | 2.7 | 2.7 | 2.4 | 2.8 | 3.4 | 3.2 |
| Fineness of foam texture | D | D | C | C | B | D | B | A | A |
| | 0.5 | 0.6 | 1.1 | 1.2 | 2.6 | 0.5 | 2.1 | 3.4 | 3.7 |
| Softness of foam | D | C | C | C | B | D | B | A | A |
| | 0.4 | 1.1 | 1.8 | 1.7 | 2.6 | 0.3 | 2.2 | 3.5 | 3.5 |
| Smoothness in the starting rinsing | D | C | C | C | B | D | B | A | A |
| | 0.3 | 1.3 | 1.9 | 1.6 | 2.5 | 0.3 | 2.1 | 3.3 | 3.8 |
| Smoothness in the end of rinsing | D | C | C | C | C | D | B | A | A |
| | 0.2 | 1.2 | 1.1 | 1.4 | 1.7 | 0.2 | 2.3 | 3.7 | 3.6 |
| Luster | C | C | A | C | C | C | A | A | A |
| | 1.5 | 1.4 | 3.5 | 1.6 | 1.8 | 1.6 | 3.3 | 3.5 | 3.5 |

*Merquat 550 (ONDEO NALCO LTD.) with 8% by weight of an effective component.
**Amount required for adjusting pH.

EXAMPLE 4

Shampoo with transparent appearance

| | (% by weight) |
|---|---|
| sodium polyoxyethylene(2) lauryl ether sulfate | 15.0 |
| cocamide MEA | 0.4 |
| lauramidopropyl betaine | 1.5 |
| polyoxyethylene(16) lauryl ether | 2.0 |
| polypropylene glycol(Mw = 400) | 0.5 |
| benzyl alcohol | 0.2 |
| polyquaternium-10 | 0.5 |
| a solution of a dimethyl diallyl ammonium chloride/ acrylamide copolymer* | 1.0 |
| malic acid | 0.8 |
| 48% by weight of a solution of sodium hydroxide | q.s. |
| disodium EDTA | 0.4 |
| perfume | trace |
| purified water | balance |

*Merquat 550 (an effective component of 8% by weight: a product from ONDEO NALCO Ltd.)

The above-described shampoo (pH=3.7) was superior in qualities such as foamability, fineness texture and softness of foam, softness and smoothness of hair both in lathering and rinsing, hair luster, elasticity, manageability after drying as well as in storage stability.

EXPERIMENT 5

Shampoo with pearlescent appearance

| | (% by weight) |
|---|---|
| sodium polyoxyethylene(2) lauryl ether sulfate | 10.0 |
| sodium lauryl sulfate | 5.0 |
| cocamide MEA | 0.8 |
| myristyl alcohol | 1.0 |
| lauramidopropyl betaine | 1.0 |
| polyoxyethylene(16) lauryl ether | 2.0 |
| ethylene glycol distearate | 2.0 |
| polypropylene glycol(Mw = 400) | 1.0 |
| polyquaternium-10 | 0.5 |
| high molecular weight dimethyl polysiloxane (d = 1000–2700) | 1.0 |
| dimethyl polysiloxane (d = 50–300) | 1.4 |
| a solution of a dimethyl diallyl ammonium chloride/ acrylamide copolymer* | 1.5 |
| malic acid | 0.8 |
| 48% by weight of a solution of sodium hydroxide | q.s. |
| eucalyptus extract (dry content of 0.2% by weight) | 0.05 |
| hydrolyzed conchiolin solution (dry content of 3% by weight) | 0.05 |
| soy extract (dry content of 0.4% by weight) | 0.05 |
| panax ginseng root extract (dry content of 3% by weight) | 0.05 |
| rice germ oil | 0.05 |
| disodium EDTA | 0.4 |
| sodium chloride | 0.2 |
| perfume | trace |
| purified water | balance |

*Merquat 550 (an effective component of 8% by weight: a product from ONDEO NALCO Ltd.)

The above-described shampoo (pH=3.7) was superior in qualities such as foamability, fineness texture and softness of foam, softness and smoothness of hair both in lathering and rinsing, hair luster, elasticity, manageability after drying as well as in storage stability.

EXPERIMENT 6

Anti-dandruff shampoo

| | (% by weight) |
|---|---|
| sodium polyoxyethylene(2) lauryl ether sulfate | 15.0 |
| cocamide MEA | 0.4 |
| lauramidopropyl betaine | 1.0 |
| polyoxyethylene(16) lauryl ether | 2.0 |
| ethylene glycol distearate | 2.0 |
| polypropylene glycol(Mw = 400) | 0.5 |
| polyquaternium-10 | 0.5 |
| high molecular weight dimethyl polysiloxane (d = 1000–2700) | 1.0 |
| dimethyl polysiloxane (d = 50–300) | 1.4 |
| a solution of a dimethyl diallyl ammonium chloride/ acrylamide copolymer* | 1.5 |
| malic acid | 0.8 |
| 48% by weight of a solution of sodium hydroxide | q.s. |
| benzalkonium chloride | 0.5 |
| disodium EDTA | 0.4 |
| perfume | trace |
| purified water | balance |

*Merquat 550 (an effective component of 8% by weight: a product from ONDEO NALCO Ltd.)

The above-described shampoo (pH=3.7) was superior in qualities such as foamability, fineness of foam texture, softness, smoothness both in washing and rinsing, hair gloss, elasticity, tenacity, manageability after drying as well as in stability.

The invention claimed is:

1. A cleansing composition comprising the following components (A) to (D') and (H):
   (A) from 1 to 50% by weight of at least one anionic surfactant selected from the group consisting of a polyoxyethylene alkyl ether sulfate and an alkyl sulfate;
   (B) from 0.03 to 0.5% by weight of a copolymer of a dialkyl diallyl ammonium salt/acrylamide;
   (C) from 0.1 to 10% by weight of a fatty acid alkanolamide and a polyoxyethylene alkyl ether;
   (D') from 0.1 to 5.0% by weight of an organic acid of hydroxycarboxylic acids; and
   (H) from 0.1 to 20% by weight of a solvent of a polypropylene glycol having a molecular weight of from 300 to 600;
   wherein the composition has a pH of 2 to 4.0 at 25° C., in 20 weight times water dilution.

2. The cleansing composition according to claim 1, wherein Component (A) is represented by the following general formula (1) and (2):

$$R^1O(CH_2CH_2O)_mSO_3M \quad (1)$$

$$R^2OSO_3M \quad (2)$$

wherein $R^1$ represents an alkyl group or an alkenyl group having 10 to 18 carbon atoms; $R^2$ represents an alkyl group having 10 to 18 carbon atoms; M represents an alkali metal, an alkaline earth metal, ammonium, alkanol amine or basic amino acid; and m represents a number of 1 to 5 in weight average.

3. The cleansing composition according to claim 1, wherein the weight ratio of Component (B) to Component (C) is 1:50 to 1:5.

4. The cleansing composition according to claim 1, further comprising (D) a cationic polymer other than Component (B).

5. The cleansing composition according to claim 1, further comprising (D) a cationic polymer other than Component (B);

wherein the weight ratio of Component (B) to Component (D) is 1:1 to 1:10.

6. The cleansing composition according to claim 1, further comprising (E) one or more conditioning components selected from the group consisting of a cationic surfactant, a silicone, an oil, and mixtures thereof.

7. The cleansing composition according to claim 1, wherein said cleansing composition is a hair washing composition.

8. The cleansing composition according to claim 1, wherein the fatty acid alkanolamide is defined by formula (I)

(I)

wherein $R^1$ C(O) is an acyl group having 8 to 22 carbon atoms, $R^2$ is hydrogen or a mono-hydroxyalkyl group having 2 to 3 carbon atoms, and $R^3$ is a mono-hydroxyalkyl group having 2 to 3 carbon atoms.

9. The cleansing composition according to claim 1, wherein said fatty acid alkanolamide is selected from the group consisting of oleicdiethanolamide, palm kernel oil fatty acid diethanolamide, coconut fatty acid diethanolamide, lauric acid diethanolamide, polyoxyethylene coconut fatty acid monoethanolamide, coconut fatty acid monoethanolamide, lauric acid isopropanolamide, lauric acid monoethanolamide, and combinations thereof.

10. The cleansing composition according to claim 1, wherein said fatty acid alkanolamide is coconut fatty acid monoethanolamide.

11. The cleansing composition according to claim 1, wherein the composition has a pH of 3 to 3.9 at 25° C., in 20 weight times water dilution.

12. The cleansing composition according to claim 1, wherein the weight ratio of Component (B) to Component (C) is 1:40 to 1:6.

13. The cleansing composition according to claim 1, further comprising (D) a cationic polymer other than Component (B);
wherein the weight ratio of Component (B) to Component (D) is 1:4 to 1:6.

14. The cleansing composition according to claim 1, further comprising Component (F) a nonionic surfactant other than Component (C).

15. The cleansing composition according to claim 1, wherein the amount of component (A) ranges from 5 to 30% by weight of the total composition.

16. The cleansing composition according to claim 1, wherein the amount of component (A) ranges from 8 to 25% by weight of the total composition.

17. The cleansing composition according to claim 1, wherein the amount of component (B) ranges from 0.05 to 0.3% by weight of the total composition.

18. The cleansing composition according to claim 1, wherein the amount of component (C) ranges from 0.3 to 5% by weight of the total composition.

19. The cleansing composition according to claim 1, wherein the amount of component (C) ranges from 0.5 to 4% by weight of the total composition.

20. The cleansing composition according to claim 1, wherein the amount of component (D') ranges from 0.2 to 3% by weight of the total composition.

21. The cleansing composition according to claim 1, wherein said organic acid is malic acid.

* * * * *